United States Patent [19]

Belikan et al.

[11] Patent Number: 5,060,634
[45] Date of Patent: Oct. 29, 1991

[54] LITHOTRIPTOR WITH REDUCED ATTENUATION X-RAY LOCATING SYSTEM

[75] Inventors: Thomas Belikan; Werner Krauss, both of Knittlingen; Helmut Wurster, Oberderdingen, all of Fed. Rep. of Germany

[73] Assignee: Richard Wolf GmbH, Knittligen, Fed. Rep. of Germany

[21] Appl. No.: 574,330

[22] Filed: Aug. 28, 1990

Related U.S. Application Data

[63] Continuation-in-part of Ser. No. 408,835, Sep. 18, 1989, and a continuation-in-part of Ser. No. 494,208, Mar. 15, 1990.

[30] Foreign Application Priority Data

Oct. 12, 1989 [DE] Fed. Rep. of Germany ....... 3934105

[51] Int. Cl.[5] ............................................. A61B 17/22
[52] U.S. Cl. ........................... 128/24 EL; 128/660.03; 378/6.2; 378/145
[58] Field of Search ................... 128/24 EL, 653, 804, 128/660.03; 378/145, 62

[56] References Cited

U.S. PATENT DOCUMENTS

| | | | |
|---|---|---|---|
| 3,891,845 | 6/1975 | English | 378/58 |
| 3,993,906 | 11/1976 | English | 378/58 |
| 4,539,989 | 9/1985 | Forssmann et al. | 128/24 EL |
| 4,705,026 | 11/1987 | Chaussy et al. | 128/24 EL |
| 4,936,291 | 6/1990 | Forssmann et al. | 128/24 EL |

FOREIGN PATENT DOCUMENTS

| | | |
|---|---|---|
| 2722252 | 11/1978 | Fed. Rep. of Germany ... 128/24 EL |
| 3503702 | 8/1986 | Fed. Rep. of Germany . |
| 3826709 | 2/1989 | Fed. Rep. of Germany . |
| 3727692 | 3/1989 | Fed. Rep. of Germany . |

OTHER PUBLICATIONS

"Dornier Nierenlithotripter", Brochure No. ZMV207-84035000 of Dornier System GmbH Medizintechnik (Jul. 1982).

Primary Examiner—Ruth S. Smith
Attorney, Agent, or Firm—Panitch, Schwarze, Jacobs & Nadel

[57] ABSTRACT

In a lithotriptor a shock wave transducer is provided with a focussing cup and with a forward section containing a coupling medium shut off by means of a diaphragm for application to a patient's body. In the wall of the cup there is mounted a locating system comprising an x-ray emitter the outlet of which is located in the coupling medium. The outlet is closed by means of a balloon which can be filled with gas and which can be evacuated. When the balloon is filled with gas, it expands in the direction of radiation of the x-rays up to or almost up to the diaphragm of the forward section.

6 Claims, 1 Drawing Sheet

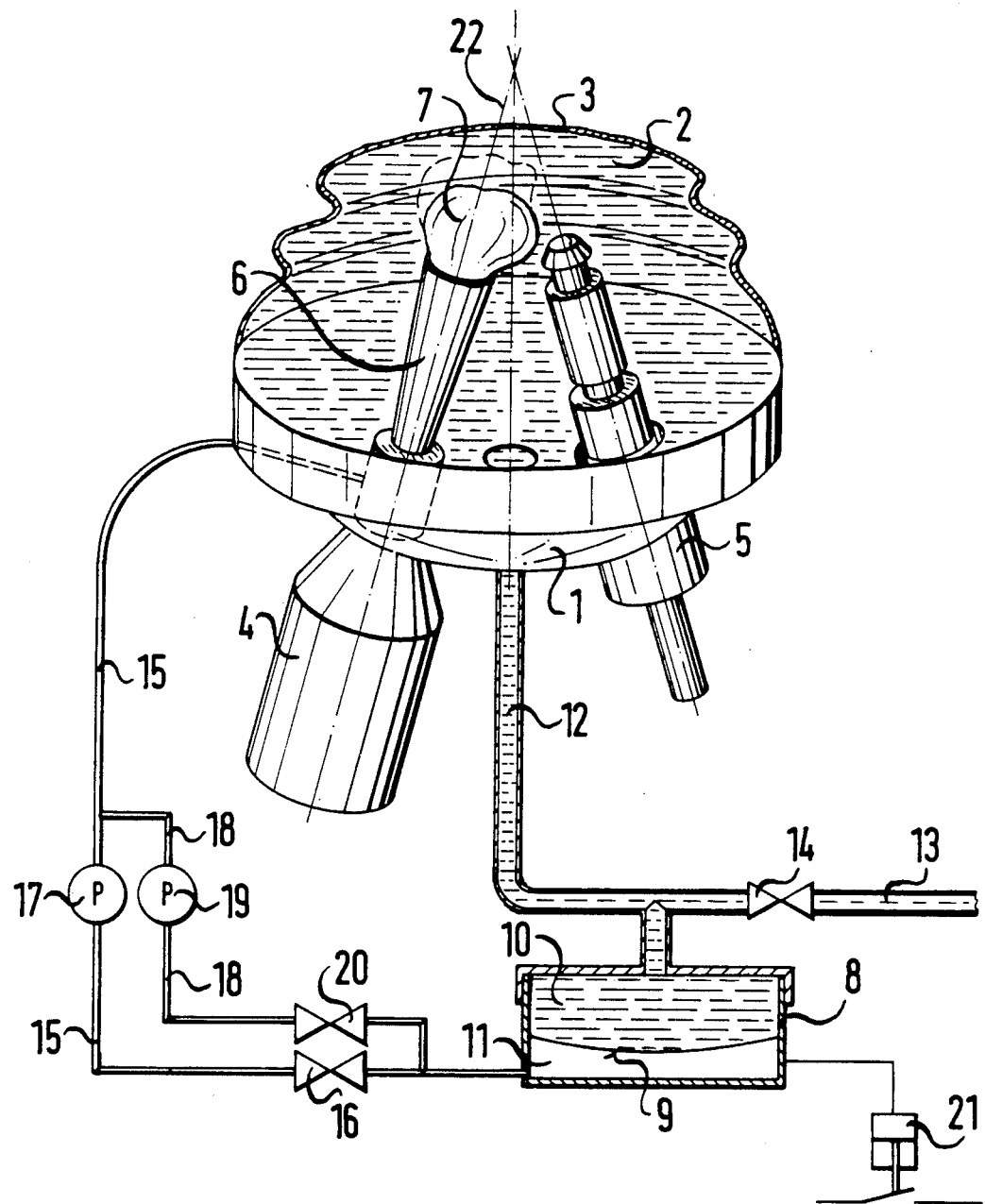

LITHOTRIPTOR WITH REDUCED ATTENUATION X-RAY LOCATING SYSTEM

CROSS-REFERENCE TO RELATED APPLICATIONS

This is a continuation in part of our copending U.S. patent application Ser. No. 408,835, filed Sept. 18, 1989, for "LITHOTRIPTOR" and our copending U.S. application Ser. No. 494,208, filed Mar. 15, 1990 for "LITHOTRIPTOR" now U.S. Pat. No. 5,060,650.

FIELD OF THE INVENTION

The invention relates to a lithotriptor comprising a shock wave transducer having a forward section containing a fluid coupling medium closed off by means of a diaphragm for application to a patient's body, the lithotriptor having a locating system for an object in the form of a concretion or tissue in the patient's body, which object is to be destroyed by means of shock waves emitted by the transducer, the locating system comprising an X-ray emitter aimed through said forward section and said diaphragm.

BACKGROUND OF THE INVENTION

The outlet of the X-ray emitter of such a lithotriptor is commonly positioned below the diaphragm to an extent that the X-rays must pass through the coupling medium, and may therefore be so attenuated thereby under some conditions that the concretion or tissue cannot reliably be located.

An object of the invention is the avoidance of that disadvantage.

SUMMARY OF THE INVENTION

According to the present invention an X-ray permeable or transparent balloon which can be filled with gas and evacuated, and which can be unfolded or expanded in said forward section in the direction of radiation of the location system is connected in a gastight manner to the outlet of the X-ray emitter in said forward section.

In operation of the lithotriptor, the balloon is filled with air or another gas until it is inflated up to, or almost up to, the diaphragm of said forward section, so that only a small quantity of the coupling medium, or none, is present between the outlet of the X-ray emitter and said diaphragm, whereby the X-rays pass only through the gas in the balloon, which has no, or only a negligible, attenuating effect upon the X-ray radiation. The balloon is evacuated after a concretion or tissue has been located, as soon as the shock wave transducer is turned on, so that the shock waves emitted thereby are unobstructed by the balloon. In order to enable the volume in the forward section occupied by the balloon to be refilled with coupling medium, automatically, after the evacuation of the balloon, a balance vessel may be provided for inflating and evacuating the balloon. Said vessel is subdivided by a flexible partition into two compartments. One compartment is connected to the coupling medium in the said forward section, whereas the other compartment is connected to the balloon for the discretionary evacuation of, or charging with gas of, the balloon. The gas compartment of the balance vessel may be connected to the balloon by way of a pipe comprising a pump and a valve, for the supply of gas to the balloon and by way of a pipe comprising a pump and a valve, for evacuating the balloon. The volume of gas withdrawn from the balloon during its evacuation is accordingly replaced automatically, by coupling medium from the balance vessel and, conversely, the coupling medium is replaced during the locating operation, by inflating the balloon with gas from the balance vessel.

BRIEF DESCRIPTION OF THE DRAWINGS

The single FIGURE is a partly isometric layout diagram of a lithotriptor according to an embodiment of the invention.

DETAILED DESCRIPTION OF THE DRAWING

A lithotriptor for the disintegration of concretions in a body cavity, or tissues therein comprises a known ultrasound shock wave transducer 1, comprising a focusing cup having a forward section comprising a receptacle containing a fluid coupling medium 2 closed off by a transparent diaphragm 3. There are mounted to a wall of said cup, a locating system comprising an X-ray emitter 4, and if desired one, or two, ultrasound locating systems 5; for locating a concretion or tissue to be destroyed by the shock waves. The corresponding X-ray intensifier (not shown) is located in a manner known in the art on the other side of the patient's body.

In accordance with the present embodiment of the invention, a balloon 7 is constructed so as to be expansible in the direction of radiation of the X-ray emitter 4, when the balloon 7 is inflated with air or another gas and so as to extend up to, or proximate to, the diaphragm 3 as indicated by a broken line. The balloon is connected in gastight fashion to the outlet of the X-ray emitter 4 or to a gas-filled tube 6 connected to the outlet of the emitter 4. The locating X-ray beam emitted by the emitter 4 accordingly traverses only gas in the balloon 7 and thereby passes directly into the bodily cavity through the transparent diaphragm, substantially without attenuation.

The balloon 7 may be inflated and evacuated, for example, by means of an air, or other gas, pump.

In the present embodiment, a balance vessel 8 is provided for inflating and evacuating the balloon 7. The vessel 8 is subdivided into coupling medium, and gas, compartments 10 and 11, respectively, by means of a flexible partition 9. The compartment 10 communicates by way of a pipe 12 with the coupling medium 2 and may be topped up with coupling medium by way of a pipe 13 in which is a valve 14.

The gas compartment 11 communicates with the balloon 7 by way of a pipe 15, a switching valve 16 and a pump 17 for delivering gas to the balloon 7 in order to inflate it. When the pump 17 is turned off and the valve 16 is closed, the balloon 7 can be evacuated by way of a pipe 18 by means of a further pump 19 and a valve 20, the gas being conveyed from the balloon 7 into the compartment 11 which accordingly expands the partition 9 forcing coupling medium from the compartment 10 into said receptacle thereby filling the vacuum created therein as a result of the evacuation of the balloon 7. Conversely, coupling medium is forced back into the compartment 10 as the balloon 7 is filled with gas.

The pressure in the compartment 11 and thus in said receptacle is monitored by means of a pressure sensor 21, by means (not shown) of which the nominal value of the gas pressure in the compartment 11 can be varied to adapt the quantity of the charge of gas in the compartment 11 and thus the distance 22 of the diaphragm 3, in accordance with the depth in the patient's body of the concretion to be treated, to the focus 23 of the transducer 1 and to secure the coupling between the diaphragm 3 and the patient's skin.

The balloon 7 is evacuated after the concretion or tissue has been located by means of said locating system and as soon as the shock wave transducer 1 has been activated, so that the shock waves emitted thereby are not obstructed by the balloon 7.

What is claimed is:

1. A lithotriptor comprising:
   a shock wave transducer for emitting shock waves for the destruction of an object in the body of a patient, said transducer having a forward section containing a fluid coupling medium closed off by a diaphragm for application to the patient's body;
   an X-ray system for locating the object to be destroyed, including an X-ray emitter mounted in a wall of the transducer and having an outlet with a direction of radiation aimed through said forward section of the shock wave transducer and said diaphragm; and
   an X-ray permeable balloon in said forward section connected in gastight fashion to the outlet of the X-ray emitter, means for expanding the balloon in the direction of radiation of said X-ray emitted by feeding a gas into the balloon, and means for evacuating gas from the balloon.

2. A lithotriptor as claimed in claim 1, wherein said balloon is connected to the outlet of the X-ray emitter by a gas fillable tube.

3. A lithotriptor as claimed in claim 2, further comprising a balance vessel for filling and evacuating said balloon, and a flexible partition dividing the interior of said vessel into first and second compartments, said first compartment being connected to said forward section and said second compartment being connected to the means for feeding gas into said balloon and to the means for evacuating gas therefrom.

4. A lithotriptor as claimed in claim 3 wherein said means for feeding and means for evacuating gas comprise first and second pipes for connecting said second compartment to said balloon, said first pipe comprising a first pump and a first valve, for supplying gas to said balloon, and said second pipe comprising a second pump and a second valve, for evacuating said balloon.

5. A lithotriptor as claimed in claim 4, wherein said first compartment is connected to said forward section for the supply of coupling medium thereto from said first compartment.

6. A lithotriptor as claimed in claim 5, further comprising a gas pressure sensor connected to said second compartment for monitoring the pressure of said second compartment and thus the flexor of said flexible partition.

* * * * *